(12) United States Patent
Sakaino et al.

(10) Patent No.: US 7,369,243 B2
(45) Date of Patent: May 6, 2008

(54) OPTICAL MEASURING APPARATUS AND OPTICAL MEASURING METHOD

(75) Inventors: Yoshiki Sakaino, Asaka (JP); Yoshihiko Abe, Asaka (JP); Kaoru Terashima, Asaka (JP)

(73) Assignee: Fujifilm Corporation, Tokyo (JP)

( * ) Notice: Subject to any disclaimer, the term of this patent is extended or adjusted under 35 U.S.C. 154(b) by 210 days.

(21) Appl. No.: 10/849,777

(22) Filed: May 21, 2004

(65) Prior Publication Data
US 2005/0002038 A1  Jan. 6, 2005

(30) Foreign Application Priority Data
May 28, 2003  (JP) .............................. 2003-150955

(51) Int. Cl.
*G01N 21/47* (2006.01)
(52) U.S. Cl. ..................................................... 356/446
(58) Field of Classification Search ........ 356/445–448, 356/433–435, 205
See application file for complete search history.

(56) References Cited

U.S. PATENT DOCUMENTS

| | | | | |
|---|---|---|---|---|
| 3,684,378 A | * | 8/1972 | Lord ............................ | 356/323 |
| 3,892,485 A | * | 7/1975 | Merritt et al. ............... | 356/339 |
| 3,917,957 A | * | 11/1975 | Ansevin et al. ............. | 250/573 |
| 4,281,897 A | * | 8/1981 | Fletcher ...................... | 356/434 |
| 4,443,695 A | * | 4/1984 | Kitamura .................... | 250/205 |
| 4,850,712 A | * | 7/1989 | Abshire ....................... | 356/602 |
| 5,204,068 A | * | 4/1993 | O'Loughlin et al. ........ | 422/180 |
| 5,340,974 A | * | 8/1994 | Zalewski ..................... | 250/205 |
| 5,519,204 A | * | 5/1996 | Rudd et al. .................. | 250/205 |
| 5,780,843 A | * | 7/1998 | Cliche et al. ................ | 250/226 |
| 5,912,454 A | * | 6/1999 | Castillo et al. .............. | 250/205 |
| 6,603,103 B1 | * | 8/2003 | Ulrich et al. ................ | 250/205 |
| 6,924,893 B2 | * | 8/2005 | Oldenbourg et al. ........ | 356/369 |
| 2002/0014577 A1 | * | 2/2002 | Ulrich et al. ................ | 250/205 |

FOREIGN PATENT DOCUMENTS

| | | |
|---|---|---|
| JP | 61-61431 U | 4/1986 |
| JP | 1-282446 A | 11/1989 |
| JP | 5-18895 A | 1/1993 |
| JP | 6-201467 A | 7/1994 |
| JP | 2001-008104 A | 1/2001 |
| JP | 2001-203969 A | 7/2001 |

* cited by examiner

*Primary Examiner*—Tarifur Chowdhury
*Assistant Examiner*—Isiaka O Akanbi
(74) *Attorney, Agent, or Firm*—Birch, Stewart, Kolasch & Birch, LLP

(57) ABSTRACT

An optical measuring apparatus comprises: an illuminating section that illuminates a first object with a first light; a light changing section that changes an intensity of the first light illuminating the first object; a light receiving device that receives a second light transmitted through or reflected from the first object; and an output section that outputs a measurement result according to i) a state of the light changing section and ii) an amount of the second light received by the light receiving device. In addition, an optical measuring apparatus comprises: the illuminating section; the light receiving device; a light receiving time changing section that changes a light receiving time of the light receiving device; and an output section that outputs a measurement result according to i) the light receiving time and ii) an amount of the second light received by the light receiving device.

24 Claims, 5 Drawing Sheets

OPTICAL MEASURING APPARATUS AND OPTICAL MEASURING METHOD

This Non-provisional application claims priority under 35 U.S.C. § 119(a) on Patent Application No(s). 2003-150955 filed in Japan on May 28, 2003, the entire contents of which are hereby incorporated by reference.

BACKGROUND OF THE INVENTION

1. Field of the Invention

The present invention relates to an optical measuring apparatus and an optical measuring method in which an object is illuminated with light, and light transmitted through or reflected from the object is measured.

2. Description of the Related Art

In an apparatus for measuring an amount of a substance by means of light measurement, an object under measurement which is horizontally placed is illuminated with light from a light source, light reflected from the object is converted into an electric signal by a light receiving device, the signal is converted to a logarithm to obtain the optical density value, and the amount of the object is obtained from the optical density value.

In an optical measuring apparatus for clinical examination, a slide in which a monolayer of a reagent is applied to a transparent support medium is used as an object under measurement, a liquid specimen such as blood is dropped on the slide, and a change of the optical density due to a reaction with the reagent layer is measured to obtain the optical density value. The optical density value is converted to a clinical value to attain a desired analysis.

In clinical examination or the like, it is required to measure the optical densities of plural components contained in blood. In an optical measuring apparatus, therefore, blood of the same person is dropped on plural slides to which different reagents are applied respectively, and the above-described measurement is conducted on each of the slides (for example, see JP-A-05-018895).

Usually, the amount of a substance is proportional to the optical density of the substance. By contrast, the common logarithm of the amount of light received by a light receiving device is proportional to the optical density, and hence the light amount is inversely proportional to the optical density. Depending on the component to be examined, namely, the amounts of light reflected from the slides are varied. In the conventional optical measuring apparatus, therefore, the light receiving device must have a wide dynamic range in which lights reflected from all the slides can be accurately received. A light receiving device having a wide dynamic range is expensive, and hence the production cost of the conventional optical measuring apparatus is inevitably increased.

SUMMARY OF THE INVENTION

The invention has been conducted in view of the above-discussed circumstances. It is an object of the invention to provide an optical measuring apparatus and method which, even in the case of a light receiving device having a narrow dynamic range, can accurately measure light transmitted through or reflected from an object, and which is therefore economical.

The optical measuring apparatus of the invention comprises: an illuminating section that illuminates a first object with a first light; a light changing section that changes an intensity of the first light illuminating the first object; a light receiving device that receives a second light transmitted through or reflected from the first object; and an output section that outputs a measurement result according to i) a state of the light changing section and ii) an amount of the second light received by the light receiving device.

The optical measuring apparatus of the invention also comprises: illuminating means for illuminating a first object with a first light; light changing means for changing an intensity of the first light illuminating the first object; a light receiving device that receives a second light transmitted through or reflected from the first object; and outputting means for outputting a measurement result according to i) a state of the light changing means and ii) an amount of the second light received by the light receiving device.

According to these configurations, the amount of light to be received by the light receiving device can be adjusted by changing the intensity of light illuminating the object. Even when the light receiving device has a narrow dynamic range, therefore, light transmitted through or reflected from the object can be accurately measured. Furthermore, an economical light receiving device having a narrow dynamic range can be used, and hence the production cost of the apparatus can be lowered.

DETAILED DESCRIPTION OF THE INVENTION

Figure 1:
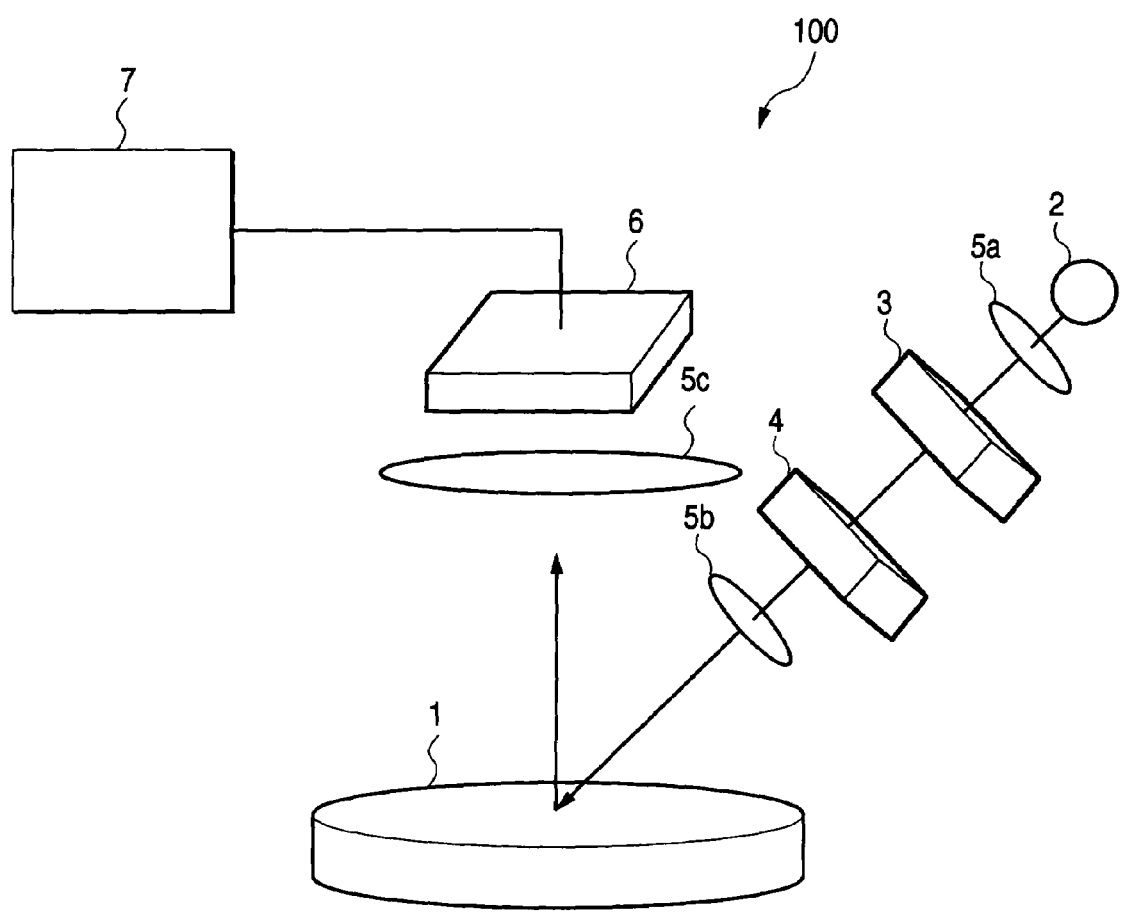
FIG. 1 is a view schematically showing the configuration of an amount measuring apparatus illustrating an embodiment of the invention.

FIG. 1 is a view schematically showing the configuration of an amount measuring apparatus illustrating an embodiment of the invention.

The amount measuring apparatus 100 comprises: a specimen placement portion 1 on which a specimen under measurement is to be placed; a light source 2 using a light emitting device such as a halogen lamp which illuminates the specimen; a light changing section 3 which changes the intensity of the light emitted from the light source 2; a wavelength changing section 4 which changes the wavelength of the light emitted from the light source 2; lenses 5a and 5b which collimate and focus the light emitted from the light source 2; a lens 5c which focuses light reflected from the specimen; an area sensor 6 serving as a light receiving device which receives the light focused by the lens 5c; and a computer 7 which controls various portions, obtains a measurement result according to the state of the light changing section 3 and the amount of the light received by the area sensor 6, and supplies the result to a display device or the like. In the embodiment, the computer 7 controls various portions. Alternatively, another computer which overall controls various portions may be separately disposed.

In the specimen placement portion 1, a slide in which a monolayer of a reagent is applied to a transparent support medium is disposed, and, when a measurement is to be conducted, a specimen such as blood is dropped on the slide.

In the light changing section 3, an attenuation filter such as a perforated plate member formed by a mesh of a metal such as stainless steel, or an ND filter is mechanically inserted between the light source 2 and the specimen and extracted therefrom, thereby changing the intensity of the light which is emitted from the light source 2 to illuminate the specimen. In the default state, the attenuation filter is inserted between the light source 2 and the specimen. In the following description, the metal mesh is a stainless steel mesh. The attenuation filter such as a perforated plate member or an ND filter may be manually inserted and extracted.

In the wavelength changing section 4, one of plural kinds of interference filters is mechanically inserted between the light source 2 and the specimen and extracted therefrom, thereby changing the wavelength of the light which is emitted from the light source 2 to illuminate the specimen. In the embodiment, the wavelength changing section 4 is disposed between the light changing section 3 and the specimen placement portion 1. Alternatively, the wavelength changing section may be disposed between the light source 2 and the light changing section 3, and the plural kinds interference filters may be manually inserted and extracted.

The area sensor 6 is a solid state imaging device such as a CCD. The area sensor receives light which is obtained as a result of reflection of the light illuminated by the light source 2 when the reagent on the slide disposed in the specimen placement portion 1 reacts with the specimen such as blood on the slide, converts the received light into an electric signal, and supplies the signal to the computer 7. The area sensor 6 can receive the light reflected from the slide, in the unit of a face. In the embodiment, therefore, the slide may be configured so that it is divided into plural areas, different kinds of reagents are applied respectively to the areas, and reflected lights respectively due to reactions between the different kinds of reagents and the blood are simultaneously received by the area sensor 6.

The computer 7 converts the electric signal output from the area sensor 6 in accordance with the amount of received light, into an optical density value on the basis of data of an analytical curve which are previously stored in a built-in memory or the like, obtains the contents and the like of various components contained in the specimen from the optical density value, and supplies the values to the display device or the like. In the case where a slide to which plural kinds of reagents are applied is used as described above, the computer 7 extracts the electric signal output from the area sensor 6 in accordance with the amount of received light, for each of the areas of the slide, and obtains the contents of components contained in the specimen for each area. The computer 7 controls the light changing section 3 and the wavelength changing section 4 in accordance with the amount of the light received by the area sensor 6 from the specimen, and the kind of the reagent to be reacted with the specimen, so that the amount or wavelength of the light emitted from the light source 2 is changed.

In the thus configured amount measuring apparatus 100, when the amount of the light reflected from the specimen is so small that it fails to be within the dynamic range of the area sensor 6, the light changing section 3 extracts the stainless steel mesh plate member or the ND filter from the space between the light source 2 and the specimen, to enhance the intensity of the light emitted from the light source 2. As a result, the amount of the light reflected from the specimen is increased so as to be within the dynamic range of the area sensor 6. Even when the area sensor 6 has a narrow dynamic range, therefore, the reflected light can be accurately received, and the accuracy of the measurement of the contents of components contained in the specimen is improved.

For example, the case of using a slide to which four kinds of reagents A, B, C, and D are applied will be considered. The amount measuring apparatus 100 obtains the amounts of lights respectively reflected from the areas to which the reagents A to D are applied. When one of the reflected light amounts fails to be within the dynamic range of the area sensor 6, the light changing section 3 conducts the insertion and extraction of the stainless steel mesh plate member or the ND filter at intervals of a constant time period. Since the lights respectively reflected from the areas have different wavelengths, the wavelength changing section 4 switches over the plural interference filters in accordance with the wavelength.

For example, the case will be described where the amounts of lights reflected from the areas to which the reagents A and B are applied are so small as not to be within the dynamic range of the area sensor 6, the amounts of lights reflected from the areas to which the reagents C and D are applied are within the dynamic range of the area sensor 6, and lights which are emitted when the reagents A to D react with blood have different wavelengths.

In this case, in the amount measuring apparatus 100, the light source 2 illuminates the slide, the area sensor 6 receives lights reflected from the areas of the slide, and the computer 7 judges whether each of the amounts of lights reflected from the areas is within the dynamic range of the area sensor 6 or not. Since the amounts of lights reflected from the areas to which the reagents A and B are applied are so small as not to be within the dynamic range of the area sensor 6, the computer 7 controls the light changing section 3 after the illumination by the light source 2 is conducted for a predetermined time period, so that the ND filter is extracted from the space between the light source 2 and the specimen. The illumination is further conducted for a predetermined time period in this extracted state, and the computer 7 then controls the light changing section 3 so that the ND filter is inserted between the light source 2 and the specimen. When the above operations are repeated, plural kinds of measurement components can be accurately measured with using the single slide.

While controlling the light changing section 3, the computer 7 then controls the wavelength changing section 4 in accordance with the kinds of the reagents A to D, so that the four kinds of interference filters are sequentially switched over. During a period when the light changing section 3 extracts the ND filter, the wavelength changing section 4 alternately switches over the interference filters for the reagents A and B with each other. During a period when the light changing section 3 inserts the ND filter, the wavelength changing section 4 alternately switches over the interference filters for reagents C and D with each other. Even when lights respectively emitted from plural kinds of components contained in the specimen have different wavelengths, therefore, the contents of the plural kinds of measurement components contained in the specimen can be measured with using the single slide.

The amount measuring apparatus 100 is configured so that the intensity of the light emitted from the light source 2 is changed, thereby enabling even a CCD having a narrow dynamic range to conduct accurate measurement. Alternatively, the light intensity may not be changed, and the exposure time of the CCD (the time period for receiving the reflected lights) may be changed by the control of the computer 7. Also in the alternative, accurate measurement can be conducted in the same manner as described above.

In the embodiment, the light source 2 illuminates the specimen, and the contents of components contained in the specimen are obtained from light reflected from the specimen. Alternatively, the contents of components contained in the specimen may be obtained from light transmitted through the specimen.

In the embodiment, light reflected from the specimen is received by the area sensor such as a CCD. Alternatively, a line sensor may be used in place of the area sensor.

As the CCD in the embodiment, it is preferable to use a so-called honeycomb CCD in which light receiving portions such as photodiodes are arranged vertically and horizontally on a semiconductor substrate at predetermined intervals, and light receiving portions in adjacent light receiving portion lines are arranged with being shifted in the line direction by about one half of the pitch of the light receiving portions in each light receiving portion line.

Figure 4:
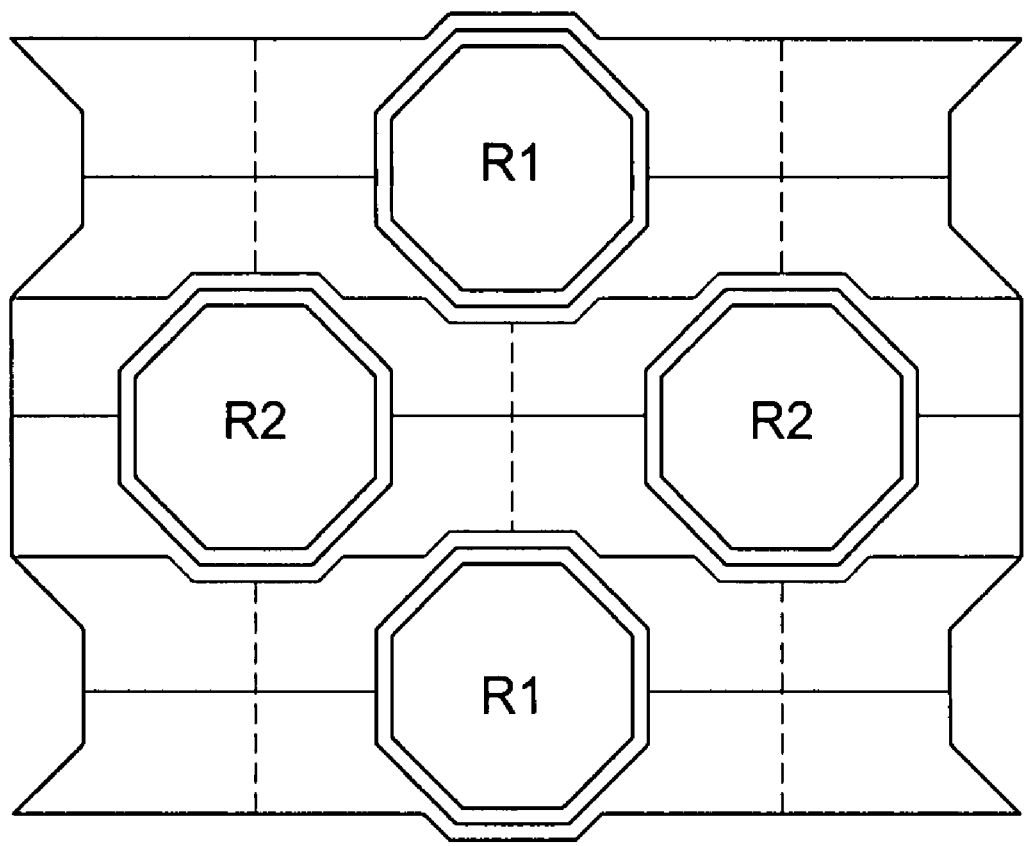
FIG. 4 is a view showing first receiving portions and second receiving portions shifted with respect to each other by substantially a half pitch.

In other words, it is preferable to use a optical measuring apparatus in which the solid state imaging device comprises: first receiving portions R1 disposed on a first line at a common pitch; and second receiving portions R2 disposed on a second line at the common pitch, the second line being adjacent to and substantially parallel to the first line, wherein the first receiving portions R1 and the second receiving portions R2 are shifted to each other along a direction of the first line by substantially a half pitch. This arrangement is shown in FIG. 4.

The specimen is not restricted to a specimen for biochemical examination such as blood. The amount measuring apparatus 100 can accurately measure also the concentrations of components contained in a specimen such as that for examination of an environmental substance or that for food examination.

In the above description, the amount measuring apparatus 100 changes in real time the light intensity in accordance with the amount of light reflected from the specimen. Alternatively, the amount measuring apparatus may measure the contents of measurement components contained in a specimen in a sequence which is preset in accordance with the measurement components. The operation in this case will be described.

When a specimen is placed in the specimen placement portion 1 and a measurement item is set, the amount measuring apparatus 100 starts a measurement process in a pattern corresponding to the measurement item. First, the computer 7 selects a light intensity to be used in the measurement from plural kinds of intensities, and controls the light changing section so as to illuminate the specimen at the selected light intensity. When the area sensor 6 receives light reflected from the specimen, the computer 7 outputs a measurement result according to the amount of the reflected light received by the area sensor 6 and also to the selected light intensity. As a result of the series of operations, the measurement component contained in the specimen can be accurately measured.

In the case where the exposure time of the CCD is changed without changing the light intensity, when a specimen is placed in the specimen placement portion 1 and a measurement item is set, the amount measuring apparatus 100 starts a measurement process in a pattern corresponding to the measurement item. First, the computer 7 conducts a control so as to illuminate the specimen. The area sensor 6 receives light reflected from the specimen, for the exposure time which is selected from plural kinds of exposure times by the computer 7. Finally, the computer 7 outputs a measurement result according to the amount of the reflected light received by the area sensor 6 and also to the selected exposure time. As a result of the series of operations, the measurement component contained in the specimen can be accurately measured.

EXAMPLE

Hereinafter, an example of the amount measuring apparatus 100 will be described.

First, a method of producing data of the analytical curve to be stored in the built-in memory of the computer 7 will be described. The data of the analytical curve are produced by the amount measuring apparatus 100 with, in place of slides, using plural kinds of standard density plates in which the respective reflection optical density values are known.

The following components were used to constitute the amount measuring apparatus 100:

Area sensor 6: CCD (8-bit B/W camera module XC-7500, a product of SONY Corporation);

Light source 2: Luminar Ace LA-150UX, a product of HAYASHI Watch-Works Co., Ltd.;

Interference filter: a filter for monochromatizing to 625 nm;

Attenuation filter: glass filter ND-25, a product of HOYA Corporation, and a filter which is produced by the inventor, and which is obtained by perforating a stainless steel mesh plate; and Computer 7: image processing apparatus LUZEX-SE, a product of NIRECO Corporation.

Standard density plates (made of ceramic) produced by FUJI Photo Equipment Co., Ltd. were used as the standard density plates. Six kinds of standard density plates: A00 having a reflection optical density of 0 to 0.05; A05 having a reflection optical density of 0.5; A10 having a reflection optical density of 1.0; A15 having a reflection optical density of 1.5; A20 having a reflection optical density of 2.0; and A30 having a reflection optical density of 3.0 were used.

A region of received light in which the measurement can be accurately conducted by the 8-bit B/W CCD (a range in which the amount of received light is 50 to 200) is defined as the range of the analytical curve. The analytical curve was prepared in the following procedure.

(1) The standard density plate A00 is used. The amount of the light from the light source 2 is adjusted by inserting the stainless steel mesh plate so that the amount of light reflected from the standard density plate A00 is about 200. With using the above six kinds of standard density plates, the relationships between the reflected light amount and the reflection optical densities are obtained. At this time, the amount of light from the light source 2 was 96 $\mu W/cm^2$ on the standard density plates.

(2) Next, the stainless steel mesh plate is extracted, and, with using the above six kinds of standard density plates, the relationships between the reflected light amount and the reflection optical densities are then obtained. At this time, the amount of light from the light source 2 was 492 $\mu W/cm^2$ on the standard density plates.

(3) The relationships between the reflected light amount and the reflection optical densities which are obtained in (1) and (2) above are formed into a graph to draw the analytical curve.

Figure 2:
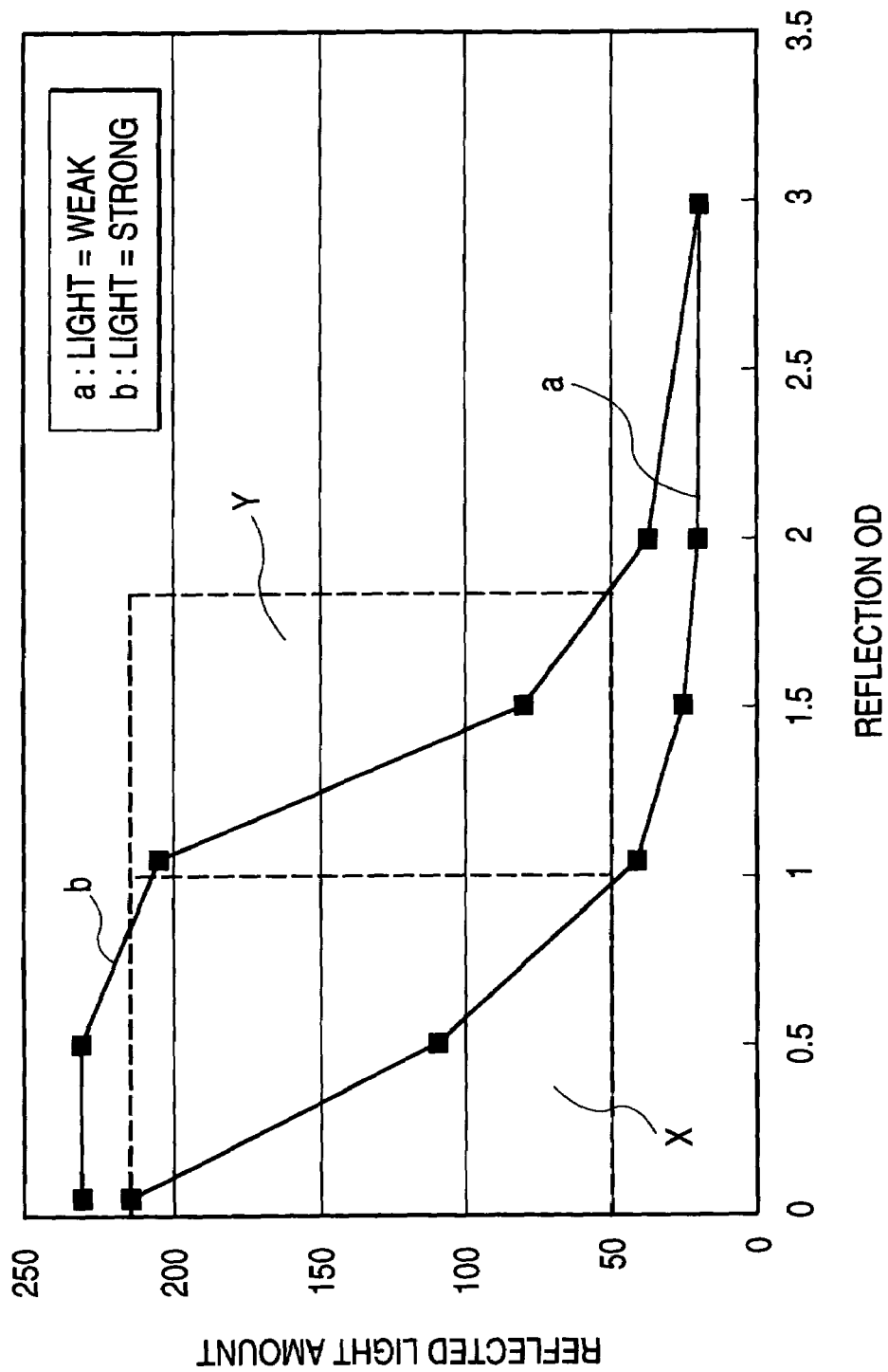
FIG. 2 is a view showing an analytical curve prepared by the amount measuring apparatus illustrating the embodiment of the invention.

FIG. 2 shows the analytical curve which was prepared in the above-described procedure.

As shown in the figure, two analytical curves respectively for the case where the light amount is large (strong) and that where the light amount is small (weak) are drawn. In a region X where, in the state where the stainless steel mesh plate is inserted, the amount of the light reflected from the specimen on the slide becomes smaller than 50 (the reflection optical density of the specimen is 0 to 0.9), the computer 7 uses the analytical curve a, and, in a region Y where, in the state where the stainless steel mesh plate is extracted, the amount of the light reflected from the specimen on the slide becomes smaller than 50 (the reflection optical density of the specimen is 0.9 to 1.8), the computer uses the analytical curve b, whereby the contents of measurement components contained in a specimen having a reflection optical density value of 0 to 1.8 can be accurately measured.

For each of the three standard density plates A05, A10, and A15, then, the standard deviation of the reflection optical density was obtained as a result of ten measurements. Results are shown in Table 1 below. The measurements were conducted with using both the stainless steel mesh plate and the ND filter as the attenuation filter.

TABLE 1

Standard deviation of reflection optical density [/10,000]

| Attenuation filter | HOYA ND-25 | | Stainless mesh | |
|---|---|---|---|---|
| | Used | Not used | Used | Not used |
| Light amount [μW/cm²] | 66 | 492 | 96 | 492 |
| A05 | 3.6 | Not measured | 4.8 | Not measured |
| A10 | 12.6 | 5.2 | 11.7 | 1.7 |
| A15 | 19.1 | 7.5 | 25.6 | 5.2 |

As shown in Table 1, when the standard deviation of the reflection optical density is obtained in the state where the attenuation filter is inserted, A05 enables the reflected light amount to be within the dynamic range of the CCD, and hence the standard deviation is $10/10,000$ or smaller, so that the measurement can be accurately conducted. However, A10 and A15 cannot cause the reflected light amount to be within the dynamic range of the CCD, and hence the accuracy is poor. Therefore, it will be noted that the accuracy is improved by extracting the attenuation filter to increase the light amount.

As described above, in all the cases of the standard density plates A05, A10, and A15, it was possible to attain the standard deviation of the reflection optical density which is $10/10,000$ or smaller, and therefore the measurement was accurately conducted. The same effect was attained in both the case where the ND filter was used, and that where the stainless steel mesh plate was used. When the stainless steel mesh plate which is more economical and less changes in time than the ND filter is used, therefore, the amount measuring apparatus 100 can be produced more economically.

Next, an experiment for quantification in clinical examination was conducted in the state where data of the analytical curve which were prepared with using plural interference filters were stored in the memory of the computer 7. In the experiment, test pieces of dry assay reagents (dry reagent for clinical examination) to be used in FUJI DRI-CHEM slides produced by FUJI Photo Film Co., Ltd., or GLU-P (measurement wavelength: 505 nm, measurement component: glucose) and TBIL-P (measurement wavelength: 540 nm, measurement component: total bilirubin) were cut into about 2 mm×4 mm. The resulting test pieces were loaded into a 5 mm×5 mm cell made of a transparent resin. An amount of 4 μL of a control serum (in this case, two kinds of serums or L and H) in which the content of a measurement component is known was dropped onto the test pieces. The reagents were reacted with the measurement component of the serum at room temperature to exhibit a color.

Figure 5:
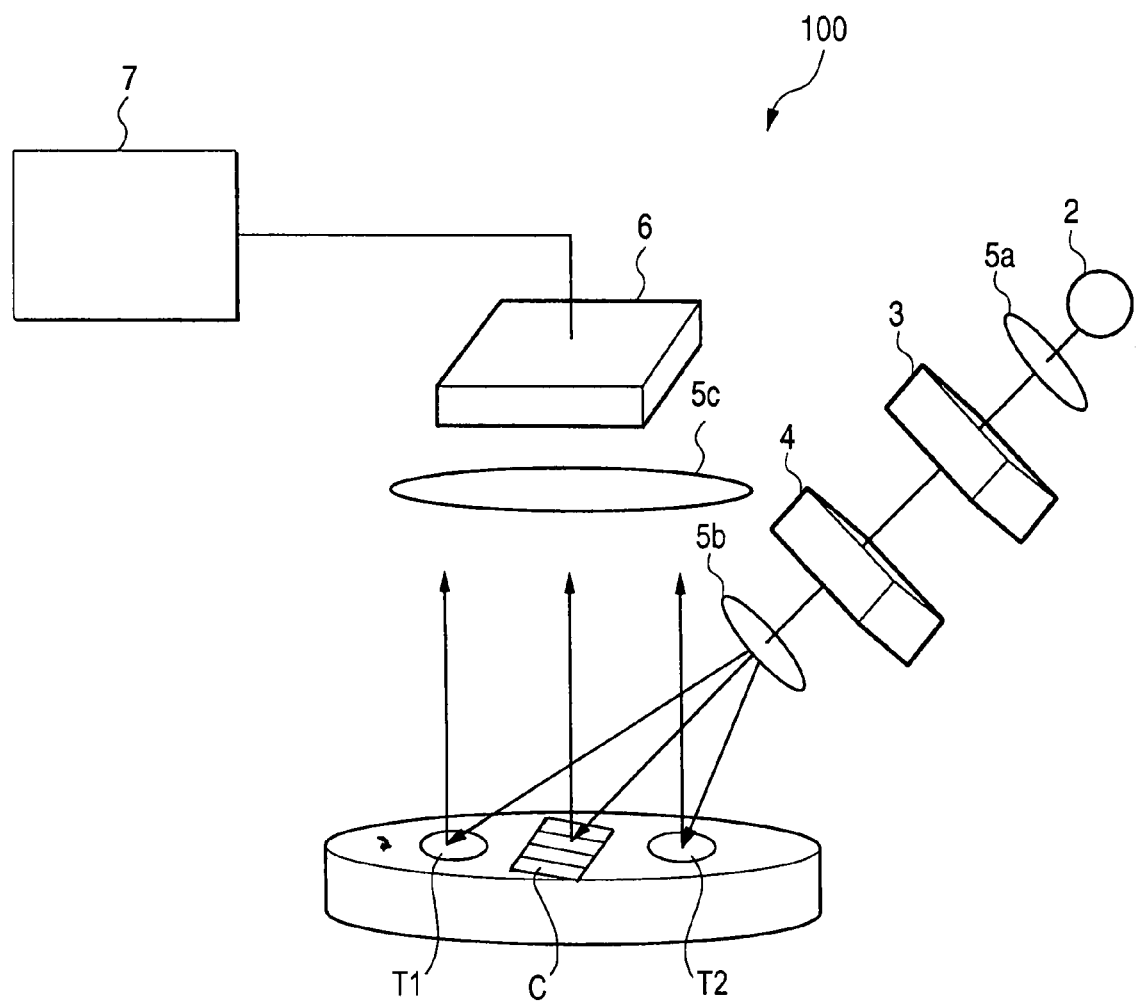
FIG. 5 is a view showing a calibration object placed in the same visual field as two test pieces.

The reflection optical density was calibrated in the following manner, as shown in FIG. 5. A calibration object C which was obtained by stepwise subjecting B/W photographic paper to uniform exposure and then developing it was cut into pieces of about 1.5 mm×2 mm. Four pieces (levels 1 to 4) of the calibration object C were arranged, and placed in the same visual field (the imageable range of the CCD) as the two test pieces T1, T2 These pieces were imaged by the CCD with using light which was monochromatized by the interference filter. In this case, the computer 7 controls the operations so that reflected light from the specimen and also the reflected light from the calibration object C are received and the optical density of the component contained in the specimen is calculated on the basis of the amount of the light reflected by the calibration object C. In the experiment, the amount and wavelength of the light illuminating the slide were sequentially changed in the sequence shown in Table 2 below, and the reflection optical density of the calibration object was set as listed in Table 3.

TABLE 2

Sequence of switching over wavelength and amount of light

| Sequence | Wavelength [nm] | Attenuation filter |
|---|---|---|
| 1 | 505 | Inserted |
| 2 | 505 | Extracted |
| 3 | 540 | Inserted |
| 4 | 540 | Extracted |

TABLE 3

Reflection optical density of calibration object

| Wavelength [nm] | Reflection optical density at each wavelength | | | |
|---|---|---|---|---|
| | Level 1 | Level 2 | Level 3 | Level 4 |
| 505 | 0.0620 | 0.9219 | 1.3941 | 1.6858 |
| 540 | 0.0677 | 0.9155 | 1.3968 | 1.6768 |

With respect to a measurement component in which the reflected light amount received by the CCD is 50 to 200 when lights of wavelengths of 505 nm and 540 nm are used in the state where the attenuation filter is inserted, the reflection optical density was obtained from the reflected light amount with using the analytical curve a shown in FIG. 2. With respect to a measurement component in which the reflected light amount is smaller than 50, the reflection optical density was obtained from the reflected light amount with using the analytical curve b shown in FIG. 2. From the reflection densities in coloration of glucose and total bilirubin which were obtained as described above, and the analytical curve data which were previously stored in the computer 7, and in which reflection densities are correlated with contents of measurement components, concentrations of glucose and total bilirubin in the serum were calculated. Results of the calculation are listed in Table 4 below.

TABLE 4

Concentration of measurement component in serum [mg/dL]

| | Control serum L | | Control serum H | |
|---|---|---|---|---|
| | Measured Value | Standard value of control serum | Measured Value | Standard value of control serum |
| Glucose | 107 | 108.4 | 312 | 319.0 |
| Total bilirubin | 1.01 | 1.07 | 5.36 | 5.49 |

As shown in Table 4, the measured values and the standard values of the control serum are substantially coincident with one another. Therefore, it was proved that even a CCD having a narrow dynamic range can accurately measure the contents of measurement components in a serum. Furthermore, the two measurement components are simultaneously measured. As compared with the conventional case where two slides respectively for GLU-P and TBIL-P are prepared and measurements are separately conducted, therefore, the measurement can be efficiently conducted. Although only two measurement components were measured in the embodiment, the concentrations of two or more measurement components can be simultaneously measured as far as two or more test pieces can be placed in the imageable range of the CCD.

Next, with respect to the standard density plates which are imaged by the CCD, the reflection optical density was obtained while changing the area (measurement area) to be used for obtaining the reflection optical density, ten measurements were conducted for each of the areas, and the standard deviation of the reflection optical density was obtained for each area. In this case, an experiment was conducted while the light from the light source 2 was monochromatized to 625 nm and the standard density plate A05 was used as the measurement target. The experiment was conducted while using two CCD lens systems including the lens 5c and respectively having magnifications of 1 and 0.33. Results of the experiment are shown in Tables 5 and 6, and FIG. 3.

TABLE 5

Standard deviation of reflection optical density (magnification of lens system of CCD: 1)

| Measurement diameter [mm] | 0.2 | 0.4 | 1 | 2 | 3 |
|---|---|---|---|---|---|
| Measurement diameter [px] | 20 | 40 | 100 | 200 | 300 |
| Measurement area [px²] | 314 | 1,256 | 7,850 | 31,400 | 70,650 |
| Standard deviation [/10,000] | 11.2 | 6.1 | 2.4 | 2.9 | 3.4 |

TABLE 6

Standard deviation of reflection optical density (magnification of lens system of CCD: 0.33)

| Measurement diameter [mm] | 0.4 | 1 | 2 | 3 | 4 |
|---|---|---|---|---|---|
| Measurement diameter [px] | 14 | 34 | 67 | 100 | 133 |
| Measurement area [px²] | 154 | 907 | 3,524 | 7,850 | 13,886 |
| Standard deviation [/10,000] | 17.1 | 4.2 | 5.9 | 4.3 | 3.5 |

Figure 3:
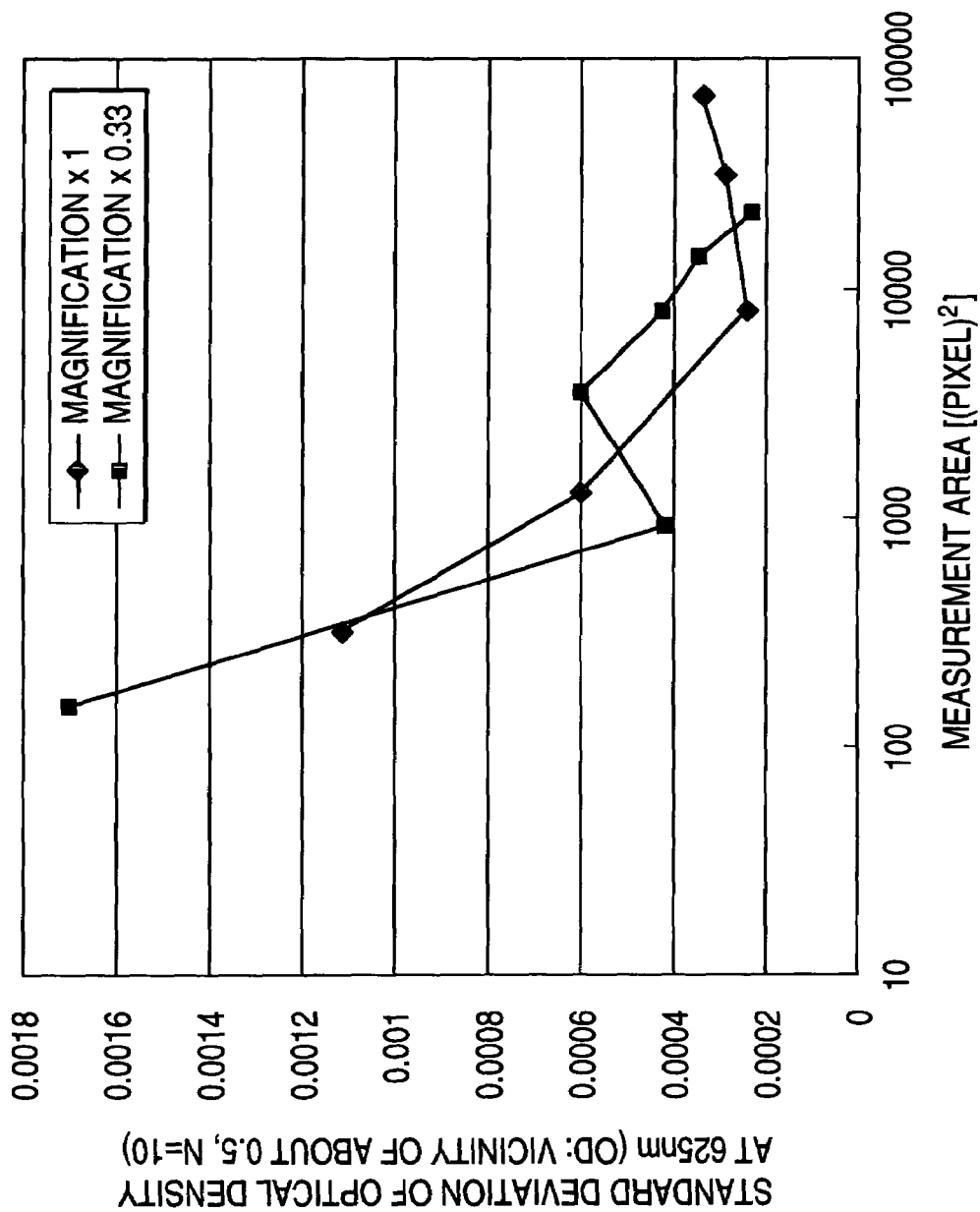
FIG. 3 is a view showing results of experiments in which, with respect to standard density plates which are imaged by a CCD, standard deviation of a reflection optical density was obtained while changing an area (measurement area) to be used for obtaining the reflection optical density.

As shown in Tables 5 and 6, and FIG. 3, it was proved that, when the size of the area on the standard density plate for obtaining the reflection optical density is about 1,000 pixels or more, the standard deviation of the reflection optical density is 10/10,000 or smaller, and the measurement accuracy is improved. In the case where four calibration objects and two test pieces are placed in the imageable range of the CCD and the measurement is then conducted as described above, when the reflection optical density is obtained on the basis of the amounts of reflected lights which are received respectively by areas of 1,000 pixels or more in each of the four calibration objects and two test pieces, it is possible to conduct the measurement more accurately.

According to the invention, it is possible to provide an optical measuring apparatus which, even in the case of a light receiving device having a narrow dynamic range, can accurately measure light transmitted through or reflected from an object, and which is therefore economical.

The entire disclosure of each and every foreign patent application from which the benefit of foreign priority has been claimed in the present application is incorporated herein by reference, as if fully set forth.

What is claimed is:

1. An optical measuring apparatus comprising:
an illuminating section that illuminates a first object with a first light;
a light changing section that changes an intensity of the first light illuminating the first object;
a light receiving device that receives a second light transmitted through or reflected from the first object;
a control device for causing the light changing section to change the intensity of the first light when an amount of the second light transmitted through or reflected from the first object is not within a dynamic range of the light receiving section; and
an output section that outputs, as a measurement result, an optical density of the first object according to i) a state of the light changing section, and ii) the amount of the second light received by the light receiving device,
wherein the illuminating section also illuminates a calibration object having a known optical density, with the first light at the same time when the first object is illuminated with the first light;
the light receiving device also receives third light transmitted through or reflected from the calibration object; and
the output section calculates the optical density of the first object, on the basis of an amount of the third light from the calibration object.

2. The optical measuring apparatus according to claim 1, wherein, when the light receiving device receives a plurality of the second lights transmitted through or reflected from a plurality of the first objects, the output section outputs a plurality of measurement results according to a plurality of amounts of the second lights.

3. The optical measuring apparatus according to claim 1, further comprising:
a wavelength changing section that changes a wavelength of the first light from the illuminating section.

4. The optical measuring apparatus according to claim 1, wherein the light receiving device is an area sensor.

5. The optical measuring apparatus according to claim 4, wherein the area sensor is a solid state imaging device.

6. The optical measuring apparatus according to claim 5, wherein the solid state imaging device receiving the second light, comprises:
first receiving portions disposed on a first line at a common pitch; and
second receiving portions disposed on a second line at the common pitch, the second line being adjacent to and substantially parallel to the first line,
wherein the first receiving portions and the second receiving portions are shifted to each other along a direction of the first line by substantially a half pitch.

7. The optical measuring apparatus according to claim 1, wherein the light changing section changes an intensity of the first light by attenuating the first light from the illuminating section by a perforated plate member.

8. The optical measuring apparatus according to claim 7, wherein the perforated plate member is a mesh formed of a metal.

9. The optical measuring apparatus according to claim 1, wherein the light changing section changes an intensity of the first light by attenuating the first light from the illuminating section by an ND filter.

10. The optical measuring apparatus according to claim 1, wherein the first object is a specimen for biochemical examination.

11. The optical measuring apparatus according to claim 1, wherein the first object is a specimen for examination of an environmental substance.

12. The optical measuring apparatus according to claim 1, wherein the first object is a specimen for food examination.

13. The optical measuring apparatus according to claim 1, further comprising a computer adapted to control the light changing section in accordance with the amount of the light received by the light receiving device from the first object, and a reagent to be reacted with the first object, so that the intensity of the light emitted from the illuminating section is changed.

14. The optical measuring apparatus according to claim 3, further comprising a computer adapted to control the light changing section and the wavelength changing section in accordance with the amount of the light received by light receiving device from the first object, and a reagent to be reacted with the first object, so that the intensity or the wavelength of the light emitted from the illuminating section is changed.

15. An optical measuring apparatus comprising:
an illuminating section that illuminates a first object with a first light;
a light receiving device that receives a second light transmitted through or reflected from the first object;
a light receiving time changing section that changes a light receiving time of the light receiving device;
a control device for causing the light changing section to change the intensity of the first light when an amount of the second light transmitted through or reflected from the first object is not within a dynamic range of the light receiving section; and
an output section that outputs, as a measurement result, an optical density of the first object according to i) the light receiving time, and ii) an amount of the second light received by the light receiving device,
wherein the illuminating section also illuminates a calibration object having a known optical density, with the first light at the same time when the first object is illuminated with the first light;
the light receiving device also receives third light transmitted through or reflected from the calibration object; and
the output section calculates the optical density of the first object, on the basis of an amount of the third light from the calibration object.

16. The optical measuring apparatus according to claim 12, wherein the light receiving device includes:
first receiving portions disposed on a first line at a common pitch; and
second receiving portions disposed on a second line at the common pitch, the second line being adjacent to and substantially parallel to the first line, the first receiving portions and the second receiving portions being shifted to each other along a direction of the first line by substantially a half pitch.

17. An optical measuring apparatus comprising:
illuminating means for illuminating a first object with a first light;
light changing means for changing an intensity of the first light illuminating the first object;
a light receiving device that receives a second light transmitted through or reflected from the first object;
control means for causing the light changing section to change the intensity of the first light when an amount of the second light transmitted through or reflected from the first object is not within a dynamic range of the light receiving section; and
outputting means for outputting, as a measurement result, an optical density of the first object according to i) a state of the light changing means, and ii) an amount of the second light received by the light receiving devices,
wherein the illuminating section also illuminates a calibration object having a known optical density, with the first light at the same time when the first object is illuminated with the first light;
the light receiving device also receives third light transmitted through or reflected from the calibration object; and
the output section calculates the optical density of the first object, on the basis of an amount of the third light from the calibration object.

18. The optical measuring apparatus according to claim 17, wherein the light receiving device includes:
first receiving portions disposed on a first line at a common pitch; and
second receiving portions disposed on a second line at the common pitch, the second line being adjacent to and substantially parallel to the first line, the first receiving portions and the second receiving portions being shifted to each other along a direction of the first line by substantially a half pitch.

19. An optical measuring apparatus comprising:
illuminating means for illuminating a first object with a first;
a light receiving device that receives a second light transmitted through or reflected from the first object;
light receiving time changing means for changing a light receiving time of the light receiving device;
a control device for causing the light changing section to change the intensity of the first light when an amount of the second light transmitted through or reflected from the first object is not within a dynamic range of the light receiving section; and outputting means for outputting, as a measurement result, an optical density of the first object according to i) the light receiving time, and ii) an amount of the second light received by the light receiving devices, wherein the illuminating section also illuminates a calibration object having a known optical density, with the first light at the same time when the first object is illuminated with the first light;

the light receiving device also receives third light transmitted through or reflected from the calibration object; and the output section calculates the optical density of the first object, on the basis of an amount of the third light from the calibration object.

20. The optical measuring apparatus according to claim 19, wherein the light receiving device includes:

first receiving portions disposed on a first line at a common pitch; and second receiving portions disposed on a second line at the common pitch, the second line being adjacent to and substantially parallel to the first line, the first receiving portions and the second receiving portions being shifted to each other along a direction of the first line by substantially a half pitch.

21. An optical measuring method comprising:

illuminating a first object with a first light of an illuminating section, the first light having an intensity which is selected from plural kinds of intensities;

receiving a second light in a light receiving device, the second light having been transmitted through or reflected from the first object;

controlling the intensity of the first light when an amount of the second light transmitted through or reflected from the first object is not within a dynamic range of the light receiving section; and outputting a measurement result from an output section according to an amount of the second light and an intensity of the first light, wherein the illuminating section also illuminates a calibration object having a known optical density, with the first light at the same time when the first object is illuminated with the first light;

the light receiving device also receives third light transmitted through or reflected from the calibration object; and the output section calculates the optical density of the first object, on the basis of an amount of the third light from the calibration object.

22. The optical measuring method according to claim 21, further comprising the step of controlling the intensity of the first light in the illuminating step in accordance with an amount of the second light received in the receiving step.

23. An optical measuring method comprising:

illuminating a first object with a first light of an illuminating section;

receiving a second light in a light receiving device, the second light having been transmitted through or reflected from the first object, for a light receiving time period which is selected from plural kinds of light receiving time periods;

controlling the intensity of the first light when an amount of the second light transmitted through or reflected from the first object is not within a dynamic range of the light receiving section; and outputting a measurement result from an output section result according to an amount of the second light and the selected light receiving time period of the second light, wherein the illuminating section also illuminates a calibration object having a known optical density, with the first light at the same time when the first object is illuminated with the first light;

the light receiving device also receives third light transmitted through or reflected from the calibration object; and the output section calculates the optical density of the first object, on the basis of an amount of the third light from the calibration object.

24. The optical measuring method according to claim 23, further comprising the step of selecting the light receiving time period by changing an exposure time.

* * * * *